United States Patent [19]

Monnier et al.

[11] Patent Number: 4,789,711
[45] Date of Patent: Dec. 6, 1988

[54] MULTIFUNCTIONAL EPOXIDE RESINS

[75] Inventors: Charles E. Monnier, Villars-sur-Glâne; Sameer H. Eldin, Fribourg; Peter Flury, Himmelried, all of Switzerland

[73] Assignee: Ciba-Geigy Corporation, Ardsley, N.Y.

[21] Appl. No.: 124,200

[22] Filed: Nov. 23, 1987

[30] Foreign Application Priority Data

Dec. 2, 1986 [CH] Switzerland ............... 4801/86

[51] Int. Cl.[4] .................................. C08G 59/32
[52] U.S. Cl. ............................... 525/507; 528/99; 528/101; 549/556; 549/560
[58] Field of Search ............ 525/507, 502; 528/99, 528/101; 549/556, 560

[56] References Cited

U.S. PATENT DOCUMENTS

| | | | |
|---|---|---|---|
| 2,910,455 | 10/1959 | Christenson | 528/101 |
| 2,965,607 | 12/1960 | Martin et al. | 260/47 |
| 2,967,161 | 1/1961 | Hart | 260/18 |
| 3,291,770 | 12/1966 | Gaylord et al. | 528/101 X |
| 3,984,376 | 10/1976 | Yokono et al. | 260/47 EP |
| 4,384,129 | 5/1983 | Zahir et al. | 528/101 X |
| 4,652,619 | 3/1987 | Nakajima et al. | 525/507 X |
| 4,677,170 | 6/1987 | Monnier et al. | |

FOREIGN PATENT DOCUMENTS

| | | | |
|---|---|---|---|
| 617979 | 4/1961 | Canada | 528/101 |
| 1149816 | 7/1983 | Canada | |
| 59-124905 | 7/1984 | Japan | |
| 823181 | 11/1959 | United Kingdom | |
| 828364 | 2/1960 | United Kingdom | |

OTHER PUBLICATIONS

A. L. Cupples et al., Adv. Chem. Ser. 92, 173 (1970).
E. A. Dzhauadyn et al., Polymer Bulletin 4, 479 (1981).

Primary Examiner—Earl Nielsen
Attorney, Agent, or Firm—Luther A. R. Hall

[57] ABSTRACT

The invention relates to compounds of the formula I

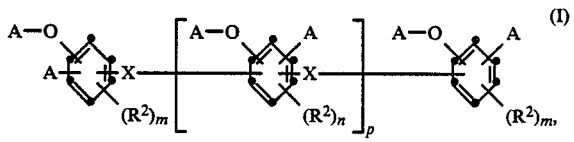

in which
A is a group

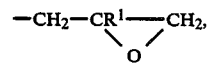

$R^1$ is hydrogen or methyl
$R^2$ is $C_1$–$C_6$-alkyl, halogen or phenyl,
X is a direct C—C bond, —$CH_2$— or —$SO_2$—,
m is 0, 1, 2 or 3, n is 0, 1 or 2 and
p is 0 or, in the case of X=—$CH_2$—, can also be an integer from 1 to 6, with the proviso that the groups —A and —O—A are in the ortho-position relative to one another.

The compounds can preferably be used as matrix resins for composite materials.

The invention also relates to the allyl glycidyl ether intermediates, from which the compounds of the formula I are as a rule prepared by epoxidation with peracids.

11 Claims, No Drawings

MULTIFUNCTIONAL EPOXIDE RESINS

The present application relates to multifunctional epoxide resins based on derivatives of biphenyl, diphenylmethane and diphenyl sulfone, to the corresponding diallyl diglycidyl ether intermediates, to mixtures containing the said multifunctional epoxide resins and curing agents, as well as to the use of these curable mixtures as adhesives or for the production of composite materials and laminates.

Multifunctional epoxide resins obtainable by epoxidation of allylphenyl glycidyl ethers are known. Thus, British Patent Specification No. 828,364 describes ethers of epoxy-substituted phenols, for example 2,2-bis-(4-epoxipropoxy-3-epoxipropylphenyl)-propane. The compound is prepared by epoxidizing 2,2-bis(4-epoxipropoxy-3-allylphenyl)-propane with peracetic acid.

In Adv. Chem. Ser., 92, 173–207 (1970), A. L. Cupples et al. describe various epoxide resins which are to be used in small quantities for the purpose of rapid curing. Inter alia, the tetraglycidyl ethers of bis-(2,4-dihydroxyphenyl)methane and of 2,2',4,4'-tetrahydroxybiphenyl are also investigated. The compounds are classed as curing relatively slowly, and this behaviour is ascribed to the high viscosity at room temperature.

In Polymer Bulletin 4, 479–485 (1981), E. A. Dzvahadvan et al. investigate the influence of the bridge groups on the reactivity and mechanical properties of various diglycidyl ethers of 4,4'-bisaromatic compounds. Tetra functional or higher-functional derivatives are not investigated.

U.S. Pat. No. 2,967,161 describes bis-(allylglycidyloxyphenyl)-alkane compounds which can be crosslinked together with unsaturated polyamides. The alkylene bridge between the phenyl radicals must have two to four C atoms.

In British Patent No. 823,181, the preparation of epoxysubstituted aromatic compounds, inter alia of biphenyl derivatives, is described. Tetra functional or higher-functional derivatives are not mentioned. The compounds are derived from allyl-substituted aromatics and are as a rule obtained by epoxidizing these intermediates with a peracid.

A selected group of multifunctional epoxide resins has now been found, which are distinguished by improved mechanical and/or rheological properties. Thus, mixtures of these resins with curing agents have as a rule low starting viscosities, which facilitates their processing or the production of highly filled systems. The cured mixtures are distinguished by a high flexural strength, good adhesive properties, especially on metals, and low water absorption.

The present invention relates to compounds of the formula I

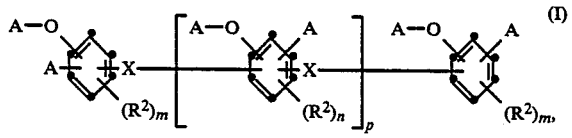

in which A is a group

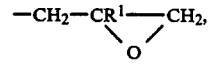

$R^1$ is hydrogen or methyl, $R^2$ is $C_1$–$C_6$-alkyl, halogen or phenyl, X is a direct C—C bond, —$CH_2$— or —$SO_2$—, m is 0, 1, 2, or 3, n is 0, 1 or 2 and p is 0 or, in the case of X=—$CH_2$—, can also be an integer from 1 to 6, with the proviso that the groups —A and —O—A are the ortho-position relative to one another. $R^1$ is preferably hydrogen. $C_1$–$C_6$-alkyl $R^2$ is straight-chain or branched, preferably straight-chain. Examples of such radicals are methyl, ethyl, n-propyl, isopropyl, n-butyl, isobutyl, n-pentyl or n-hexyl. Methyl is preferred. Halogen $R^2$ is fluorine, chlorine, bromine or iodine, and chlorine and bromine, especially chlorine, are preferred. The index m is preferably 0 or 1, but with very particular preference 0. The index n is preferably 0 or 1, but with very particular preference 0. The index p is preferably 0. Those compounds of the formula I are particularly preferred in which m, n and p are 0.

The bridge group X is preferably a direct C—C bond or —$SO_2$—. With very particular preference, the bridge is a direct C—C bond.

Those compounds of the formula I are particularly preferred in which the radicals —O—A are always in the orthoposition or para-position relative to the —X— bridge.

Those compounds of the formula I are very particularly preferred in which the radicals —O—A are always in the orthoposition relative to the —X— bridge.

The compounds of the formula I can be obtained by epoxidizing the corresponding allyl glycidyl ethers or methallyl glycidyl ethers with peracid. These intermediates are novel and likewise included in the scope of the present invention.

The invention therefore also relates to compounds of the formula II

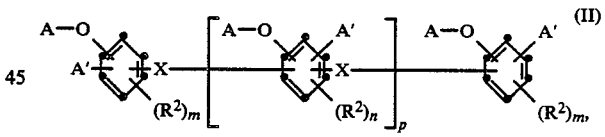

in which A is a group

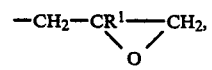

$R^1$ is hydrogen or methyl,
A' is a group —$CH_2$—$CR^1$=$CH_2$, $R^2$ is $C_1$–$C_6$-alkyl, halogen or phenyl, X is a direct C—C bond, —$CH_2$— or —$SO_2$—, m is 0, 1, 2 or 3, n is 0, 1 or 2 and p is 0 or, in the case of X=—$CH_2$—, can also be an integer from 1 to 6, with the proviso that the groups —A' and —O—A are in the ortho-position relative to one another.

The compounds of the formula II are prepared in a manner known per se by reacting the corresponding allylphenols with an epihalohydrin or β-methylepihalohydrin, in particular with epichlorohydrin.

The allylphenols are prepared in a manner known per se by etherifying the corresponding phenols and a subsequent Claisen rearrangement. Examples of such reactions are described in EP-A No. 13,258.

The polyphenols used as starting materials for the preparation of the compounds of the formula II are known, and most of them are commercially available. Examples of such compounds are 4,4'-dihydroxybiphenyl, 4,4'-dihydroxydiphenylmethane, 4,4'-dihydroxydiphenyl sulfone or novolaks based on phenol and formaldehyde.

The peracids used for epoxidizing the etherified compounds II are especially organic peracids, for example performic acid, peracetic acid, persuccinic acid, perbenzoic acid, m-chloroperbenzoic acid and monoperphthalic acid. The organic peracids can be employed as such or formed in situ, for example from aliphatic or aromatic carboxylic acids, carboxylic acid anhydrides, carboxylic acid esters, acid chlorides or ketene and hydrogen peroxide. For the in-situ formation of the peracids, aliphatic or aromatic mono- or di-carboxylic acids or their anhydrides, such as formic acid, acetic acid, propionic acid, succinic ahydride, benzoic acid or phthalic acid, and hydrogen peroxide are preferably used, if appropriate with an addition of acid catalysts, such as sulfuric acid or alkali metal salts. The epoxidation of the adducts is preferably carried out in the presence of performic acid or peracetic acid, preformed or generated in situ. If desired, inorganic peracids, such as permolybdic acid, pervanadic acid or pertungstic acid, can also be used. The epoxidizing agent (peracid) is advantageously used in a quantity of at least 1 mol per (meth)allyl group present, and preferably in an excess, for example a 20–200% molar excess.

The etherification of the starting phenols or of the allylphenols and the epoxidation of the products is with advantage carried out in the presence of inert organic solvents and, in the case of the epoxidation, if appropriate with an addition of buffer substances, such as sodium acetate or sodium hydrogen phosphate. Examples of suitable solvents are aliphatic or aromatic hydrocarbons which may be halogenated, such as chloroform, dichloromethane, benzene, toluene and chlorobenzene, ethers such as diethyl ether, diisopropyl ether, dioxane and tetrahydrofuran, and also alkyl carboxylates such as ethyl acetate and n-butyl acetate. Halogenated, especially chlorinated, aliphatic hydrocarbons are the preferred solvents; chloroform is particularly preferred. The reaction temperatures are in general between $-10°$ and $+100°$ C., preferably between $10°$ and $60°$ C.

A further preparation method of the compounds of the formula I starts from the corresponding polyallylated bisphenols. The allyl groups on the nucleus and the allyloxy groups are then epoxidized by epoxidation with peracids. Examples of such reactions are given in Japanese Published Application No. 59-124,905. This process variant gives derivatives of particularly low halogen content.

The polyepoxides obtainable according to the invention are pure substances, which are substantially free of chloride ions and alkali metal ions. They are suitable for the production of cured products, especially as matrix resins for composite materials.

The invention therefore also relates to mixtures comprising (a) a polyepoxide of the formula I and
(b) a curing agent for component (a).

Mixtures of different polyepoxides obtainable according to the invention and/or curing agents can also be used here. Suitable curing agents (b) are in general any desired epoxide resin curing agents, for example cyanamide, dicyandiamide, polycarboxylic acid, polycarboxylic acid anhydride, polyamines, polyaminoamides, adducts of amines and polyepoxides, and polyols.

Examples of suitable polycarboxylic acids and their anhydrides are phthalic anhydride or tetrahydro- and hexahydrophthalic anhydride, and also the acids corresponding to the abovementioned anhydrides.

Examples of polyamines, which are suitable curing agents, are aliphatic, cycloaliphatic, aromatic and heterocyclic polyamines, such as hexamethylenediamine, diethylenetriamine, m-xylylenediamine, bis-(4-aminocyclohexyl)-methane, m- and p-phenylenediamine, bis-(4-aminophenyl)-methane, bis-4-aminophenyl sulfone and aniline/formaldehyde resins. Examples of suitable polyaminoamides are those which have been prepared from aliphatic polyamines and dimerized or trimerized unsaturated fatty acids.

Polyol curing agents (b) are especially mononuclear or polynuclear aromatic polyols, including novolaks, such as resorcinol, hydroquinone, 2,6-dihydroxytoluene, pyrogallol, 1,1,3-tris-(hydroxyphenyl)-propane, bis-(4-hydroxyphenyl)methane, 2,2-bis-(4-hydroxyphenyl)-propane, bis-4-hydroxyphenyl sulfone and 4,4'-dihydroxybiphenyl as well as novolaks of formaldehyde or acetaldehyde and phenol, chlorophenol or alkylphenols having up to 9 C atoms in the alkyl moiety, in particular cresol novolaks and phenol novolaks.

The preferred curing agents are polycarboxylic acid anhydrides, such as tetrahydro- and hexahydro-phthalic anhydride, and also aromatic polyamines, in particular bis-(4- aminophenyl)-methane, bis-4-aminophenyl sulfone and m- or p-phenylenediamine, and very especially polyol curing agents based on novolaks, in particular cresol novolaks or phenol novolaks.

The mixtures according to the invention can also contain further conventional additives, especially (c) an accelerator and/or (d) further epoxide resins.

Compounds known per se can likewise be used as the accelerators (c). Examples are: complexes of amines, especially tertiary amines, such as monoethylamine, with boron trifluoride or boron trichloride, tertiary amines such as benzyldimethylamine, urea derivatives such as N-4-chlorophenyl N',N'-dimethylurea (monuron), and substituted or unsubstituted imidazoles such as imidazole or 2-phenylimidazole. The preferred accelerators (c) are tertiary amines, especially benzyldimethylamine, and imidazoles, especially 2-phenylimidazole or 2-ethyl-4-methylimidazole.

The further epoxide resins (d) are especially those with, on average, more than one group A, bound to a hetero atom, for example to an S and preferably an O atom or N atom, such as are described above.

With particular preference, the component (d) used is a diglycidyl ether, which may have been advanced, of dihydric phenols or cyclohexanols, especially 2,2-bis-(4-hydroxyphenyl)propane, 2,2-bis-(dibromo-4-hydroxyphenyl)-propane, bis-(4-hydroxyphenyl)-methane, bis-(4-hydroxycyclohexyl)-methane or 2,2-bis-(4-hydroxycyclohexyl)-propane, polyglycidyl ethers of novolaks or tetraglycidylated 4,4'-diaminodiphenylmethane. Diglycidyl ethers, which may have been advanced, of bisphenol A, tetrabromobisphenol A or bisphenol F, polyglycidyl ethers of phenol/formaldehyde novolaks or cresol/formaldehyde novolaks or mixtures thereof are very particularly preferred.

The components (b) and (c) are employed in the usual effective quantities, i.e. quantities sufficient for curing the mixtures according to the invention. The ratio of the components (a), (b), (c) and, if appropriate, (d) depends on the nature of the compounds used, on the required curing rate and on the desired properties of the end product, and it can readily be determined by those skilled in the epoxide resin curing field. If the curing agent (b) is an amine, 0.75 to 1.25 equivalents of amine hydrogen are normally employed per 1 epoxide equivalent. In the case of polycarboxylic acid curing agents or polycarboxylic acid anhydride curing agents, 0.4 to 1.1 equivalents of carboxyl groups or anhydride groups are usually employed per 1 epoxide equivalent. If polyphenols are used as the curing agent, 0.75 to 1.25 phenolic hydroxyl groups are advantageously employed per 1 epoxide equivalent. Accelerators (c) are in general used in quantities of 0.1 to 5 percent by weight, relative to the epoxide resins (a) and, if appropriate, (d).

If desired, reactive diluents, for example styrene oxide, butyl glycidyl ether, 2,2,4-trimethylpentyl glycidyl ether, phenyl glycidyl ether, cresyl glycidyl ether or glycidyl esters of synthetic, highly branched, mainly tertiary aliphatic monocarboxylic acids can be added to the curable mixtures for reducing the viscosity. As further conventional additives, the mixtures according to the invention can also contain plasticizers, extenders, fillers and reinforcing agents, for example bituminous coal tar, bitumen, textile fibres, glass fibres, asbestos fibres, boron fibres, carbon fibres, mineral silicates, mica, quartz powder, hydrated aluminium oxide, bentonites, kaolin, silica aerogel or metal powders, for example aluminium powder or iron powder, and also pigments and dyes, such as carbon black, oxide pigments and titanium dioxide, flame proofing agents, thixotropic agents, flow control agents such as silicones, waxes and stearates, some of which are also used as mould-release agents, adhesion promoters, antioxidants and light stabilizers.

The mixtures according to the invention are used, for example as adhesives or for the production of cured products, such as composite materials and laminates, but especially as matrix resins for composite materials. They can be used in a formulation adapted to the particular specific field of application, in the unfilled or filled state, for example as paints, coating compositions, finishes, moulding compounds, dipping resins, casting resins, impregnating resins, laminating resins, matrix resins and adhesives.

The curing of the mixtures according to the invention can be carried out in one or two stages, in a manner known per se. Curing of the mixtures according to the invention is in general effected by heating to temperatures between 80° and 200° C., especially 100° and 180° C.

The cured products prepared from the polyepoxides according to the invention are distinguished by good mechanical, thermal, electrical and chemical properties.

The invention is illustrated in more detail by the examples which follow. Parts are parts by weight.

(A) PREPARATION OF THE INTERMEDIATES (A1) 3,3'-Diallylbiphenyl 4,4'-diglycidyl ether (a) 3,3'-Diallyl-4,4'-dihydroxybiphenyl

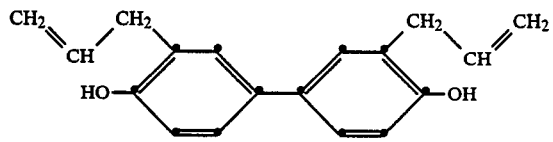

26.63 g (0.1 mol) of biphenyl 4,4'-diallyl ether dissolved in 27 ml of toluene, 0.11 g of sodium carbonate and 0.43 g of LiCl are introduced into a 50 ml round-bottom flask with cooler, thermometer and stirrer and are heated to 188°–192° C., the toluene distilling off. After a reaction time of 2 hours, the reaction mixture is cooled down, taken up in chloroform and washed with water. The organic phase is dried and concentrated, 20.50 g (77%) of 3,3'-diallyl-4,4'-dihydroxybiphenyl being isolated.

NMR (CDCl$_3$) 3.5 d 4H (allyl—CH$_2$), 5.0–5.3 m 4H (CH$_2$/ =CH), 5.8–6.25 m 2H (CH$_2$=CH—) 6.75–7.4 d×d 6H (aromatic H).

IR: KBr 3,000–3,200 broad (—OH), 1,630, 1,610, 1,500, 1,400, 1,240 cm$^{-1}$.

(b) 3,3'-Diallylbiphenyl 4,4'-diglycidyl ether

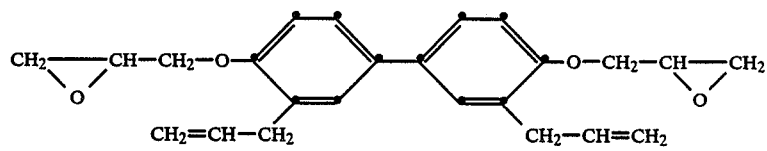

53.27 g (0.200 mol) of 3,3'-diallyl-4,4'-dihydroxybiphenyl, 272.70 g (2.93 mol) of epichlorohydrin and 3.44 g of tetramethylammonium chloride are introduced into a 750 ml sulfonation flask with cooler thermometer and stirrer, and are heated for 4 hours at 115° C. This gives a clear, yellowish solution.

The reaction mixture is then cooled down and 37.90 g (0.471 mole) of 50% sodium hydroxide solution are added dropwise at 45°–60° C., with simultaneous azeotropic distillation. The reaction mixture is allowed to react until water is no longer eliminated. After completion, the reaction mixture is filtered, rendered neutral with about 200 ml of water and 1N HCl, dried over Na$_2$SO$_4$, filtered and concentrated. This gives 77.3 g of 3,3'-diallylbiphenyl 4,4'-diglycidyl ether of an epoxide content of 5.02 equivalents/kg (95%) and a viscosity of 1,520 mPas/25° C.

IR (film) 3,000–3,300 weak, 3,030–2,800, 1,640, 1,600, 1,500, 1,240 cm$^{-1}$.

NMR (CDCl$_3$) 2.75–3.0 m 4H

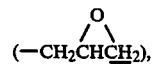

(—CH$_2$CHC̲H$_2$), 3.25–3.5 m 4H (—C̲H$_2$CH=CH$_2$) 3,75–4.3 m 6H

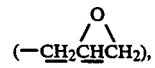

(—C̲H$_2$C̲HCH$_2$), 4.75–5.25 m 4H (—CH$_2$CH=CH$_2$) 5.75–6.25 m 2H (CH$_2$CH=CH$_2$), 6.75–7.50 m 6H (aromatic H).

(A2) 3,3'-Diallyldiphenylmethane 4,4'-diglycidyl ether

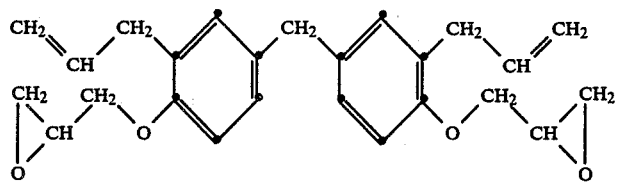

114.47 g (0.408 mole) of 3,3'-diallylbisphenol F (para, para), 7.04 g of tetramethylammonium chloride and 556.30 g (5.967 mol) of epichlorohydrin are introduced into a 1.5 litre sulfonation flask with stirrer, cooler and dropping funnel, and are heated for 4 hours at 115° C. The reaction mixture is then cooled down to 60° C. At this temperature, 77.30 g (0.960 mol) of 50% sodium hydroxide solution are added dropwise in the course of about 3 hours, the resulting water of reaction being distilled off in vacuo. After completion, the reaction mixture is filtered, and the filtrate is washed with 2×250 ml of water, dried over Na$_2$SO$_4$, filtered and concentrated. This gives 154.59 g (96.55% of theory) of a yellow, clear oil of viscosity 394 mPas/25° C. and an epoxide content of 4.48 equivalents/kg (87.96% of theory).

IR (film) 3,000–3,300 weak, 3,080–2,800, 1,640, 1,610, 1,500, 1,250, 1,170, 1,030, 920 cm$^{-1}$ $\overline{M}_n$ 412; $\overline{M}_w$ 426.

(A3) 3,3'-Diallyldiphenylmethane 2,2'-diglycidyl ether

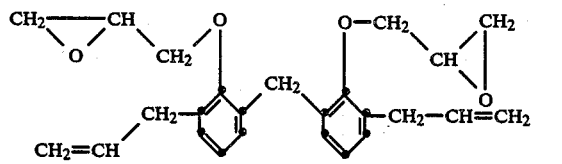

140.18 g (0.5 mol) of o,o'-diallyl-bisphenol F, 681.14 g (6.74 mol) of epichlorohydrin and 8.04 g of 50% tetramethylammonium chloride are introduced in a 1.5 litre sulfonation flask with stirrer, cooler, thermometer and dropping funnel, and heated for 4 hours at 111° C. The reaction mixture is then cooled down to 52°–56° C. and 94.67 g (1.18 mol) of 50% sodium hydroxide solution are added dropwise in the course of 3 hours, with continuous azeotropic removal of water at the same time. After the end of the water removal, the reaction mixture is filtered through a Seitz filter, and the filtrate is then washed with water and 1N HCl until neutral, dried over Na$_2$SO$_4$ and concentrated, 184.77 g (94.15% of theory) of 3,3'-diallyldiphenylmethane 2,2'-diglycidyl ether of an epoxide content of 4.212 equivalents/kg (82.66% of theory) and a viscosity of 395 mPas/25° C. being obtained.

IR (film) 3,500–3,300 (OH) 1,640, 1,450, 1,250, 1,080, 1,020, 910 cm$^{-1}$ $\overline{M}_n$ 369; $\overline{M}_w$ 382.

(A4) 3,3'-Diallyldiphenyl sulfone 4,4'-diglycidyl ether

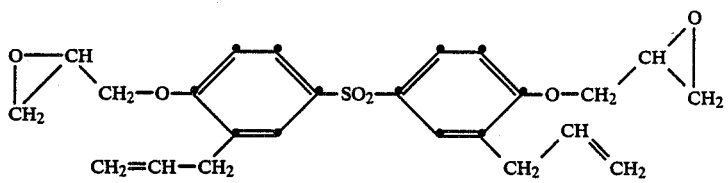

300.00 g (0.91 mol) of 3,3'-diallyl-4,4'-dihydroxydiphenyl sulfone and 1,238.37 g (13.28 mol) of epichlorohydrin are introduced into a 2.5 litre sulfonation flask with water separator, stirrer, vacuum head, thermometer and dropping funnel, and heated to 60° C. 15.65 g of 50% tetramethylammonium chloride solution are then added and the mixture is heated for 4 hours at 110°–112° C. The reaction mixture is cooled down to 50°–55° C. and 172.10 g (2.13 mol) of 50% sodium hydroxide solution are added dropwise, the water of reaction being distilled off azeotropically at the same time. The reaction mixture is allowed to react until water no longer separates out. The reaction mixture is then filtered and the filtrate is washed with 5% HCl until neutral, dried over Na$_2$SO$_4$ and concentrated at 60° C.

This gives 400.60 g (99.7% of theory) of a viscous resin n 40° C.=2,410 mPas) of an epoxide content of 3,581 equivalents/kg (79.23%).

IR (film) 3,500–3,300, 3,080–2,900, 1,640, 1,650, 1,490, 1,310, 1,250, 1,150–1,100, 1,020, 920, 830 cm$^{-1}$.

NMR (CDCl$_3$) 2.5–4.5 m~10H

4.2–6.0 m 10H (allyl-), 6.7–8.0 m 6H (aryl).

$M_n$ 420; $M_w$ 433.

(A5) 3,3-Diallylbiphenyl 2,2'-diglycidyl ether

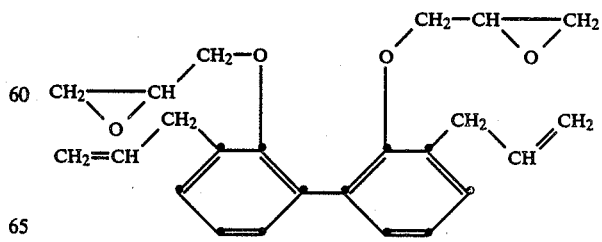

151.83 g (0.57 mol) of 3,3'-diallyl-2,2'-dihydroxybiphenyl, 777.20 g (8.34 mol) of epichlorohydrin and 9,80 g of 50% tetramethylammonium chloride solution are introduced into a 1.5 litre sulfonation flask with stirrer, cooler and dropping funnel, and heated to 118° C. After a reaction time of 4 hours, the reaction mixture is cooled down to 60° C. and, in vacuo and with simultaneous continuous removal of the water of reaction, 108.02 g (1.34 mol) of 50% sodium hydroxide solution are added dropwise in the course of 1 hour. The reaction mixture is allowed to react for approximately a further 3 hours. The salt formed is then filtered off over a filter aid, and the filtrate is diluted with toluene, washed three times with water and NaHSO$_4$ solution, dried over Na$_2$SO$_4$ and concentrated. This gives 197.7 g (91.63% of theory) of a mobile resin (n$_{25}$: 560 mPas) of an epoxide content of 4.061 equvalents/kg.

IR (film) 3,500–3,300 (broad), 3,150–2,860, 1,640, 1,440, 1,200, 1,210, 1,020, 910, 840, 760 cm$^{-1}$ NMR (CDCl$_3$) 2.2–2.6 m, 4H (—OC$\underline{H}_2$CH), 2.8–3.0 m 2H 8.230 equivalents/kg (84.47% of theory) and a viscosity of 280 mPas/80° C.

IR (Film) 3,500–3,300, 3,030–2,800, 1,740, 1,610, 1,470, 1,230, 1,130, 1,020 cm$^{-1}$ NMR (CDCl$_3$) 2.5–3.0 m about 8H

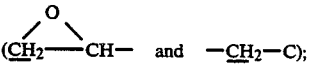

3.1–3.5 m 4H

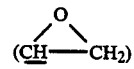

4.0–4.5 m about 4H (O—C$\underline{H}_2$—CH) 6.75–7.5 m 6H (aromatic H).

(B2) 3,3'-Diglycidyldiphenylmethane 4,4'-diglycidyl ether

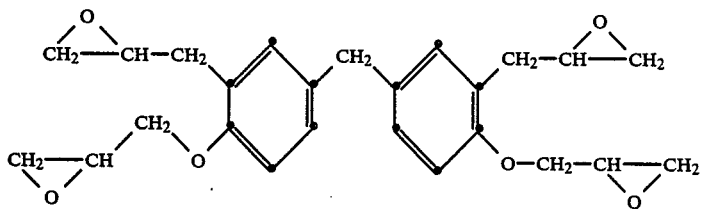

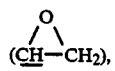

3.5–4.5 m 8H (C$\underline{H}_2$—CH═CH$_2$ and O—CH$_2$—), 5.0–5.2 m 4H (CH$_2$═C$\underline{H}$); 5.8–6.2 m 2H (—C$\underline{H}$═CH$_2$); 6.8–7.2 m 6H (aromatic H)
$\overline{M}_n$ 352; $\overline{M}_w$ 359.

(B) Preparation of the tetraglycidyl compounds (B1) 3,3'-Diglycidylbiphenyl 4,4'-diglycidyl ether

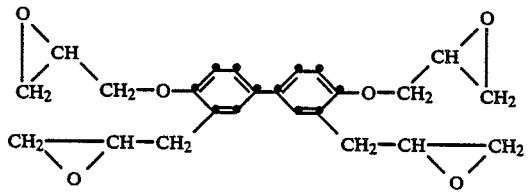

70.00 g (0.185 mol) of 3,3'-diallylbiphenyl 4,4'-diglycidyl ether (Example A1) and 2.99 g of sodium acetate in 20 ml of chloroform are introduced into a 350 ml sulfonation flask with stirrer, cooler, thermometer and dropping funnel. 80.56 g (0.39 mol) of 40% peracetic acid are added dropwise at room temperature in the course of about 2 hours. After the addition has ended the reaction mixture is stirred for a further 3 hours, 200 ml of chloroform are then added and the organic phase is washed several times with water until neutral, dried over Na$_2$SO$_4$, filtered and concentrated in vacuo. This gives 70.45 g (92.77% of theory) of 3,3'-diglycidylbiphenyl 4,4'-diglycidyl ether of an epoxide concent of 139.45 g (0.355 mol) of 3,3'-diallyl-bisphenol F 4,4'-diglycidyl ether (Example A2) in 20 ml of CHCl$_3$ and 5.70 g of sodium acetate are introduced into a 350 ml sulfonation flask with stirrer, cooler and dropping funnel. 142.60 g (0.753 mol) of 40% peracetic acid are added dropwise at 30° C. in the course of 5–6 hours. After the end of the dropwise addition, the reaction mixture is stirred for about a further minutes and then washed with water (2×500 ml), 20 g of Na$_2$SO$_3$ are added to the organic phase and the latter is stirred until there is no longer any peroxide in the reaction mixture. The reaction mixture is washed once more with water, dried over Na$_2$SO$_4$ and concentrated. This gives 131.80 g (84.47% of theory) of a highly viscous resin of an epoxide content of 7.66 equivalents/kg (81.31%) and a viscosity of 2,877 mPas/40° C.

IR (film) 3,500–3,300, 2,050–2,800, 1,740, 1,610, 1,500, 1,250, 1,130, 1,040, 920, 830 cm$^{-1}$ NMR (CDCl$_3$) 2.5–3.0 m~8H (O—CH$_2$—, aromatic —CH$_2$); 3.0–3.5 m 4H

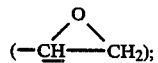

3.5–4.5 m 8H

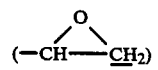

6.6–7.3 d×d (J=16 Hz) 6H (aromatic H).
$\overline{M}_n$ 420; $\overline{M}_w$ 450.

(B3) 3,3'-Diglycidyldiphenylmethane 2,2'-diglycidyl ether

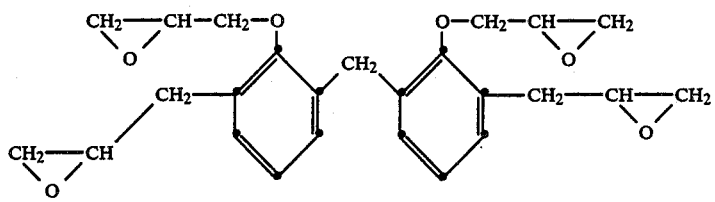

170.0 g (0.433 mol) of 3,3'-diallyldiphenylmethane 2,2'-diglycidyl ether (Example A3), 50 ml of chloroform and 6.98 g of sodium acetate are introduced into a 750 ml sulfonation flask with stirrer, thermometer, cooler and dropping funnel. 174.06 g (0.919 mol) of 40% peracetic acid are added dropwise at about 30° C. in the course of about 2 hours, the reaction being slightly exothermic. After the dropwise addition has ended, the reaction mixture is kept at this temperature for a further 4 hours, then washed with NaCl solution, 10% sodium sulfite solution and water, dried over $Na_2SO_4$ and concentrated. This gives 148.12 g (80.50% of theory) of the tetraepoxide of an epoxide content of 7.489 equivalents/kg (79.78% of theory) and a viscosity of 2,178 mPas/40° C.

IR (film) 3,850, 3,020–2,960, 1,460, 1,250, 1,090, 1,020 cm$^{-1}$ $\overline{M}_n$ 374; $\overline{M}_w$ 387.

(B4) 3,3'-Diglycidyldiphenyl sulfone 4,4'-diglycidyl ether

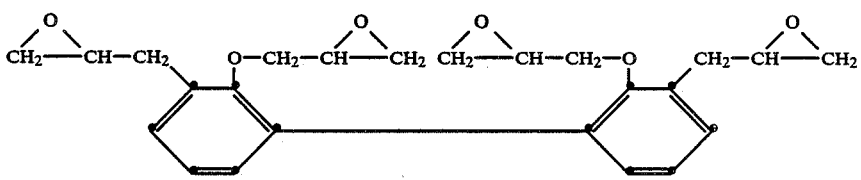

376.15 g (0.85 mol) of 3,3'-diallyldiphenyl sulfone 4,4'-diglycidyl ether (Example A4), 13.80 g of sodium acetate and 380 ml of chloroform are introduced into a 1.5 liter sulfonation flask with stirrer, thermometer, cooler and dropping funnel. 370.06 g (1.80 mol) of 40% peracetic acid are added dropwise at 25°–30° C. in the course of 3–4 hours, the reaction mixture warming up slightly. After the end of the dropwise addition, the reaction mixture is allowed to react for a further 8 hours at this temperature, then taken up in chloroform and washed with 1 liter of 2% NaOH until neutral, and the organic phase is separated off, freed of peroxide by means of 250 g of $Na_2SO_3$, filtered and concentrated at 60° C. in vacuo. This gives 311.1 g (77.13% of theory) of a viscous resin of an epoxide content of 6.040 equivalents/kg (71.65%) and a viscosity of 1,245 mPas/80° C.

IR (film) 3,500–3,300, 3,060–2,950, 1,750, 1,600, 1,490, 1,300, 1,250, 1,100, 1,020, 830 cm$^{-1}$ NMR (CDCl$_3$) 2.5–3.5 m ~8H

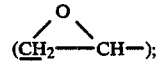

3.0–3.5 m 4H

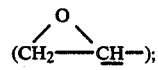

3.5–4.5 m 8H (OCH$_2$ and aryl-CH$_2$); 5.0–6.0 m (a little residual allyl group educt); 6.8–8.0 m 6H (aryl H). $\overline{M}_n$ 450; $\overline{M}_w$ 481.

(B5) 3,3'-Diglycidylbiphenyl 2,2'-diglycidyl ether

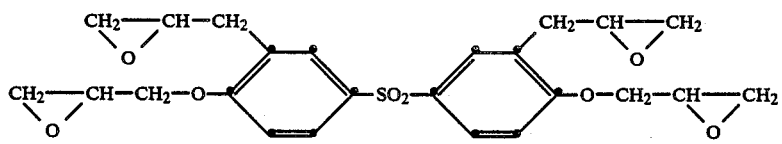

1,892.24 g (0.50 mol) of 3,3'-diallyl-2,2'-diglycidyloxybiphenyl (Example A5) and 8.10 g of sodium acetate are dissolved in 100 ml of chloroform in a 750 ml sulfonation flask with stirrer, thermometer, cooler and dropping funnel. 217.77 g (1.061 mol) of 40% peracetic acid are added dropwise at a temperature of 40°–50°C. in the course of 4–5 hours. After the dropwise addition, the reaction mixture is allowed to react fully for approximately one further hour. The reaction mixture is then diluted with 500 ml of chloroform, washed until neutral with 2×500 ml of H$_2$O and 250 ml of NaHCO$_3$, dried over Na$_2$SO$_4$ and freed of peroxide by means of Na$_2$SO$_3$, filtered and concentrated. This gives 196.83 g (95.83%) of a slightly reddish, viscous resin of an epoxide content of 7.058 equivalents/kg (72.31% of theory) and a viscosity of 5,450 mPas/40° C.

IR (film) 3,500–3,300, 3,060–2,860, 1,740, 1,440, 1,250, 1,210, 1,020 cm$^{-1}$

NMR (CDCl$_3$) 2.0–4.5 m 20H (methylene-H+methine-H), 6.8–7.6 m 6H (aromatic H)

$\overline{M}_n$ 371; $\overline{M}_w$ 389.

(C) Application Examples (C1) 100 parts of the 3,3'-diglycidyldiphenyl sulfone 4,4'diglycidyl ether prepared to Example (B4) are mixed with 29.9 parts of diaminodiphenylmethane.

This mixture has an initial viscosity of 820 mPas (at 80° C., measured by an Epprecht viscometer).

This mixture is cured under the following conditions: 4 hours at 80° C., 4 hours at 140° C. and 6 hours at 180° C.

The flexural strength of a sample cured in this way is 131.1 N/mm² (measured according to DIN 53 435).

The tensile shear strength of the sample cured in this way is 6.5 N/mm² (measured according to ISO 4587) and the water absorption after storage for four days at room temperature is 0.59% by weight.

(C2) 100 parts of the 3,3'-diglycidylbiphenyl 4,4'-diglycidyl ether prepared according to Example B1) and 40.7 parts of diaminodiphenylmethane are mixed with one another.

The initial viscosity of this mixture is 130 mPas (at 80° C., measured by an Epprecht viscometer).

This mixture is cured as indicated in Example (C1).

The flexural strength of the sample cured in this way is 108.4 N/mm² (measured according to DIN 53 435) and the bending angle is 36.4°.

The tensile shear strength of a sample cured in this way is 6.2 N/mm² (measured according to ISO 4587) and the water absorption after storage for four days at room temperature is 0.60% by weight.

What is claimed is:

1. A compound of the formula I

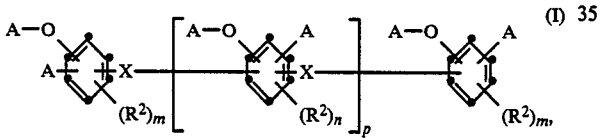

in which
A is a group

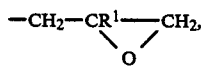

$R^1$ is hydrogen or methyl
$R^2$ is $C_1$-$C_6$-alkyl, halogen or phenyl,
X is a direct C—C bond, —CH$_2$— or —SO$_2$—,
m is 0, 1, 2 or 3, n is 0, 1 or 2 and
p is 0 or, in the case of X=—CH$_2$—, can also be an integer from 1 to 6, with the proviso that the groups —A and —O—A are in the ortho-position relative to one another.

2. A compound of the formula I according to claim 1, wherein $R^1$ is hydrogen.

3. A compound of the formula I according to claim 1, wherein m and n are 0 or 1.

4. A compound of the formula I according to claim 1, wherein p is 0.

5. A compound of the formula I according to claim 1, wherein m, n and p are 0.

6. A compound of the formula I according to claim 1, wherein X is a direct C—C bond or —SO$_2$—.

7. A compound of the formula I according to claim 1, wherein the radicals —O—A are always in the ortho-position or para-position relative to the —X— bridge.

8. The compound of the formula I according to claim 7, wherein the radicals —O—A are always in the ortho-position relative to the —X— bridge.

9. A compound of the formula II

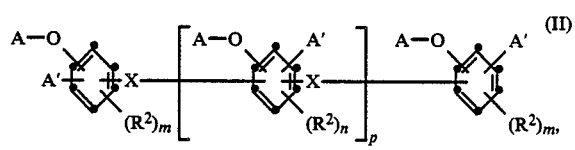

in which
A is a group

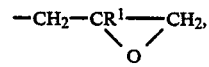

$R^1$ is hydrogen or methyl
A' is a group —CH$_2$—CR$^1$=CH$_2$, $R^2$ is $C_1$—$C_6$ alkyl, halogen or phenyl,
X is a direct C—C bond, —CH$_2$— or —SO$_2$—,
m is 0, 1, 2 or 3, n is 0, 1 or 2 and
p is 0 or, in the case of X=—CH$_2$—, can also be an integer from 1 to 6, with the proviso that the groups —A' and —O—A are in the ortho-position relative to one another.

10. A mixture comprising
(a) a polyepoxide of the formula I according to claim 1 and
(b) a curing agent for component (a).

11. A cured product obtainable by curing the mixture according to claim 10.

* * * * *